United States Patent [19]

Katoh et al.

[11] Patent Number: 5,789,618
[45] Date of Patent: Aug. 4, 1998

[54] SYNTHETIC METHOD FOR A HALOGEN-CONTAINING CONDENSATION PRODUCT

[75] Inventors: Eisaku Katoh; Osamu Ishige, both of Hino, Japan

[73] Assignee: Konica Corporation, Japan

[21] Appl. No.: 671,486

[22] Filed: Jun. 27, 1996

[30] Foreign Application Priority Data

Jul. 3, 1995 [JP] Japan .................................. 7-167387
Feb. 28, 1996 [JP] Japan .................................. 8-040861

[51] Int. Cl.$^6$ .................. C07C 231/02; C07D 231/10
[52] U.S. Cl. .................. 564/140; 548/369.4; 548/370.1; 548/370.4; 548/371.1; 560/21; 560/44; 560/100; 564/98; 564/158; 564/166; 564/169; 564/138; 564/139; 546/290
[58] Field of Search .......................... 564/138, 139, 564/140, 98, 158, 166, 169; 560/21, 44, 100; 548/369.4, 370.1, 370.4, 371.1; 546/290

[56] References Cited

U.S. PATENT DOCUMENTS

| | | | |
|---|---|---|---|
| 4,260,803 | 4/1981 | Petersen | 560/108 |
| 4,871,484 | 10/1989 | Fiege et al. | 260/408 |
| 5,514,530 | 5/1996 | Merkel et al. | 430/544 |

OTHER PUBLICATIONS

Europeach Search Report EP 96 30 4918 and one page Annex and Abstract 96304918.4, 1994.
Patent Abstracts of Japan, vol. 94, No. 010 7 JP-A-06 293723, 1994.

Primary Examiner—Shailendra Kumar
Attorney, Agent, or Firm—Jordan B. Bierman; Bierman, Muserlian and Lucas

[57] ABSTRACT

A method for synthesizing a halogen-containing condensation product, the method comprising the step of:

reacting a compound represented by Formula (I) with a compound represented by Formula (II) or (III) in the presence of a halogenating agent whereby dehydration condensation and halogenation are carried out.

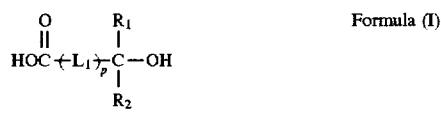

Formula (I)

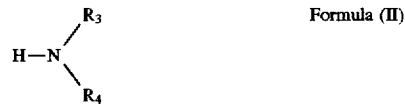

Formula (II)

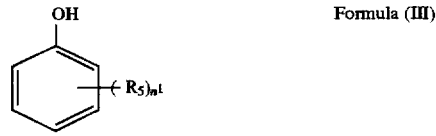

Formula (III)

9 Claims, No Drawings

SYNTHETIC METHOD FOR A HALOGEN-CONTAINING CONDENSATION PRODUCT

FIELD OF THE INVENTION

The present invention relates to a method for synthesizing a halogen-containing condensation product useful for medicines, dyes, synthetic fibers and photographic agents, and particularly to a method for synthesizing an intermediate of a functional coupler for photographic materials.

BACKGROUND OF THE INVENTION

In the synthesis of an amido group-containing compound from a carboxylic acid and an amine as starting materials, a method for preparing an acid chloride from the carboxylic acid and then reacting the acid chloride with the amine or a method for preparing an acid anhydride from the carboxylic acid and then reacting the acid anhydride with the amine is generally known. However, these methods are troublesome in that an additional procedure for preparing the acid chloride or the acid anhydride from the carboxylic acid is necessary. Particularly, in the preparation of the acid anhydride, two molecular carboxylic acids are necessary to synthesize one molecular amido group-containing compound, and the other one molecular carboxylic acid is stoichiometrically useless. This is disadvantageous in synthesizing the amido group-containing compound employing an expensive carboxylic acid.

The acid chloride or acid anhydride is a reactive compound, and when a reactive substituent (for example, a hydroxy group) such as a nucleophilic group is present in a molecule of a carboxylic acid derivative, an intramolecular or intermolecular reaction occurs, resulting in poor yield of the objective product.

In order to reduce steps of the synthesizing procedures, a direct amidation method is possible which employs DCC for a condensation agent, for example, in reaction of a carboxyl group with an amine. However, in the method employing DCC, temperature adjustment is relatively difficult, and excessive heating causes side reaction due to DCC, resulting in poor yield. Further, DCC needs to be treated carefully, in order to prevent a rash on the skin. DCC has another problem in that DCC is expensive and dicyclohexylurea produced as a by-product needs to be discarded carefully in view of environmental problems. In view of the above, a direct amidation method without employing DCC has been demanded in the art.

A 1-hydroxy-2-naphthoamide derivative is a compound widely used as a coupler in color photography, and particularly, its derivative having a halogenomethylaryloxy group in a 4-position is an important compound for synthesizing a compound such as a DIR coupler which releases a useful agent such as a development inhibitor on reaction with a developing agent. In the synthesis of the 1-hydroxy-2-naphthoamide derivative, amidation preparing an amido group from a carboxyl group and halogenation preparing a halogenomethyl group from a hydroxymethyl group have been separately carried out, as described in Japanese Patent O.P.I. Publication Nos. 57-15423/1982, 60-214358/1985 and 5-45813/1993. That is, the amidation has been carried out by synthesizing a phenylester from a carboxy-containing compound and then reacting the ester with an amine at higher temperature or by reacting a carboxy-containing compound with an amine in the presence of a condensation agent such as DCC above described, followed by halogenation employing thionylchloride, phosphorus pentachloride or hydrobromic acid. The above synthesis method has problems in that many synthesis steps are required. For example, the synthesis method is troublesome, in that when amidation is carried out by way of the phenylester, additional procedures to synthesize the phenylester are necessary, higher temperature is necessary in the procedure, and phenol produced during the procedure must be removed under reduced pressure. Further, a waste solution containing the resulting phenol by-product, needs to be carefully discarded in view of environmental problems. Therefore, the above described synthetic method is not useful.

Further, when DCC is employed, there are problems as described above that reaction conditions need to be carefully controlled to prevent side reaction. DCC needs to be treated carefully. DCC is expensive and dicyclohexylurea as a by-product needs to be discarded carefully in view of environmental problems. Therefore, a synthetic method of a condensation product without employing DCC has been eagerly sought.

SUMMARY OF THE INVENTION

Accordingly, an object of the invention is to solve the above problems and to synthesize the objective product with a simple procedure and with good yield, wherein an intermediate needs not be isolated, and no special consideration is needed for treatment of a reagent used or a by-product produced.

DETAILED DESCRIPTION OF THE INVENTION

The above objects of the invention can be attained by the followings:

1. A method for synthesizing a halogen-containing condensation product, wherein dehydration condensation and halogenation are simultaneously carried out in the presence of a halogenating agent.

2. A method for synthesizing a halogen-containing condensation product, wherein, in reaction of a compound represented by the following Formula (I) with a compound represented by the following Formula (II) or a compound represented by the following Formula (III), dehydration condensation and halogenation are carried out in the presence of a halogenating agent:

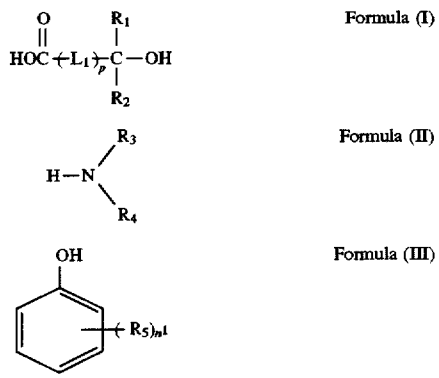

wherein $R_1$ through $R_5$ independently represent a hydrogen atom or a substituent; $L_1$ represents a linkage group, p represents 0 or 1; and $n^1$ represents an integer of 0 to 5; provided that when $n^1$ represents 2 or more, $R_5$ may be the same or different or two adjacent $R_5$ may combine with each other to form a ring. The foregoing reaction comprises substitution of the hydroxy group of $-C(R_1)(R_2)-OH$ by a halogen at a low temperature; thereafter, the amidation or esterification (depending upon whether Formula (II) or (III) is used) is conducted at a higher temperature.

3. The method for synthesizing a halogen-containing condensation product of 2 above, wherein the compound represented by Formula (I) is a compound represented by the following Formula (IV) or (V):

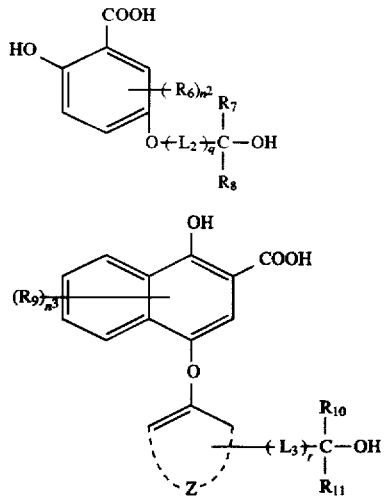

Formula (IV)

Formula (V)

wherein $R_6$ through $R_{11}$ independently represent a hydrogen atom or a substituent; $n^2$ represents an integer of 0 to 3, provided that when $n^2$ represents 2 or more, $R_6$ may be the same or different or two adjacent $R_6$ may combine with each other to form a ring; $n^3$ represents an integer of 0 to 5; provided that when $n^3$ represents 2 or more, $R_9$ may be the same or different or two adjacent $R_9$ may combine with each other to form a ring; $L_2$ and $L_3$ independently represent a linkage group; q and r independently represent 0 or 1; and Z represents an atomic group necessary to form an aromatic group or an aromatic heterocyclic group.

4. The method for synthesizing a halogen-containing condensation product, wherein, in reaction of a compound represented by the following Formula (VI) with an amine compound represented by the following Formula (VII) or a phenol compound represented by the following Formula (VIII), dehydration condensation and halogenation are carried out in the presence of a halogenating agent:

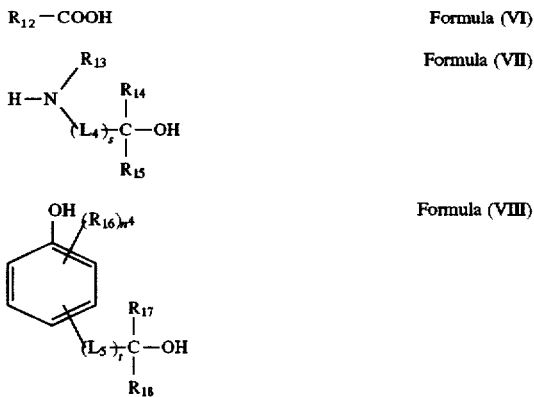

Formula (VI)

Formula (VII)

Formula (VIII)

wherein $R_{12}$ through $R_{18}$ independently represent a hydrogen atom or a substituent; $n^4$ represents an integer of 0 to 3, provided that when $n^4$ represents 2 or more, $R_{16}$ may be the same or different or two adjacent $R_{16}$ may combine with each other to form a ring; $L_4$ and $L_5$ independently represent a linkage group; and s and t independently represent 0 or 1.

The present invention will be detailed below.

In a compound represented by Formula (I), (II) or (III) in the invention, $R_1$ through $R_5$ independently represent a hydrogen atom or a substituent, and the substituent preferably includes an alkyl group or an aryl group. The example of the alkyl group includes methyl, ethyl and cyanoethyl, and the example of the aryl group includes phenyl and 4-dodecylphenyl. In Formula (II), the alkyl group represented by $R_3$ and $R_4$ includes methyl, dodecyl and ethoxycarbonylethyl, and the aryl group represented by $R_3$ and $R_4$ includes phenyl, 2-tetradecyloxyphenyl and 2-chloro-5-dodecyloxycarbonylphenyl. Of these, preferably $R_1$, $R_2$ and $R_3$ independently represent a hydrogen atom and $R_4$ preferably represents a substituted phenyl group having 10 or more carbon atoms. In Formula (III), the substituent represented by $R_5$ includes an alkyl group, an aryl group, a halogen atom, a nitro group, a cyano group, an acylamino group, a carbamoyl group, an alkylsulfonyl group, an arylsulfonyl group, a sulfamoyl group, a sulfonylamino group and a heterocyclic ring. $n^1$ represents an integer of 0 to 5, provided that when $n^1$ represents 2 or more, $R_5$ may be the same or different or two adjacent $R_5$ may combine with each other to form a ring. Particularly, it is preferable that the two adjacent $R_5$ combine with each other to form a naphthalene ring with a benzene ring in the Formula. In Formula (I), the linkage group represented by $L_1$ includes an alkylene group such as ethylene or methylene and an arylene such as phenylene, each of which may have a substituent. p represents 0 or 1.

In the invention the compound represented by Formula (I) is preferably a compound represented by the following Formula (IV) or (V).

In Formula (IV) or (V), $R_6$ through $R_{11}$ independently represent a hydrogen atom or a substituent, and the substituent represented by $R_7$, $R_8$, $R_{10}$ or $R_{11}$ preferably includes an alkyl group or an aryl group. The example of the alkyl group includes methyl, ethyl and cyanoethyl, and the example of the aryl group includes phenyl and 4-dodecylphenyl. Of these, $R_7$, $R_8$, $R_{10}$ and $R_{11}$ independently represent preferably a hydrogen atom. The substituent represented by $R_6$ or $R_9$ includes an alkyl group, an aryl group, a halogen atom, a nitro group, a cyano group, an acylamino group, a carbamoyl group, an alkylsulfonyl group, an arylsulfonyl group, a sulfamoyl group, a sulfonylamino group and a heterocyclic ring. Preferably, $R_6$ and $R_9$ independently represent a hydrogen atom. In Formula (IV), $n^2$ represents an integer of 0 to 3, provided that when $n^2$ represents 2 or more, the adjacent two $R_6$ may combine with each other to form a ring. q represents 0 or 1. In Formula (V), the linkage group represented by $L_3$ includes an alkylene group such as ethylene or methylene and an arylene such as phenylene, each of which may have a substituent. r represents 0 or 1. $n^3$ represents an integer of 0 to 5, and preferably 0 to 3. When $n^3$ represents 2 or more, the $R_9$ may combine with each other to form a ring. Z represents an atomic group necessary to form an aromatic group or an aromatic heterocyclic group, and the example includes 1-phenyl-3-methyl-5-pyrazolyl, 1-(4-nitrophenyl)-3-undecyl-5-pyrazolyl and 2-pyridyl.

In Formulae (VI) through (VIII), $R_{12}$ through $R_{18}$ independently represent a hydrogen atom or a substituent, and the substituent preferably includes an alkyl group or an aryl group. The example of the alkyl group includes methyl, ethyl and cyanoethyl, and the example of the aryl group includes phenyl, 4-dodecylphenyl and 3-pyridyl. In Formula (VII), the alkyl group represented by $R_{13}$ includes methyl, dodecyl and ethoxycarbonylethyl, and the aryl group represented by $R_{13}$ includes phenyl, 2-tetradecyloxyphenyl and 2-chloro-5-dodecyloxycarbonylphenyl. Of these, preferably $R_{13}$ represents a hydrogen atom. In Formulae (VII) and (VIII). $R_{14}$ and $R_{15}$ or $R_{17}$ and $R_{18}$, independently represent a hydrogen atom or a substituent, and the substituent represented by $R_{14}$, $R_{15}$, $R_{17}$ or $R_{18}$ preferably includes an alkyl group or an aryl group. The example of the alkyl group includes methyl, ethyl and cyanoethyl, and the example of the aryl group includes phenyl and 4-dodecylphenyl. Of these, preferably $R_{14}$ and $R_{15}$, $R_{17}$ and $R_{18}$ independently represent a hydrogen atom. The substituent represented by $R_{16}$ includes an alkyl group, an aryl group, a halogen atom, a nitro group, a cyano group, an acylamino group, a carbamoyl group, an alkylsulfonyl group, an arylsulfonyl group, a sulfamoyl group, a sulfonylamino group and a heterocyclic ring, but is not limited thereto. Preferably, $R_{16}$ represents a hydrogen atom. The linkage group represented by $L_4$ and $L_5$ includes an alkylene group such as ethylene or methylene and an arylene such as phenylene, each of which may have a substituent. s and p independently represent 0 or 1. In Formula (VIII), $n^4$ represents an integer of 0 to 4, provided that when $n^4$ represents 2 or more, $R_{16}$ may be the same or different or two adjacent $R_{16}$ may combine with each other to form a ring. Particularly, it is preferable that the two adjacent $R_5$ combine with each other to form a naphthalene ring with a benzene ring in the Formula.

The halogenating agent used in the invention includes phosphorous trichloride, thionylchloride, phosphorus oxychloride, phosphoric pentachloride, phosphorous tribromide, and phosphorus oxybromide. The halogenating agent in the invention is preferably phosphorous trichloride in that the objective product can be obtained with good yield, which is one object of the invention, and side reactions are reduced. The theoretical amount of the halogenating agent used is an amount equivalent to the sum of the number to dehydration-condensate a starting material and the number of a hydroxy group to be substituted with halogen. However, the amount of the halogenating agent is preferably one to two times the theoretical amount, since synthesis reaction is smoothly completed and treatment to remove the halogenating agent after reaction is reduced. The amount of the halogenating agent is more preferably 1.05 to 1.5 times the theoretical amount.

In the synthetic method of the invention, the presence of a tertiary amide or a tertiary amine as a catalyst gives a further better yield of the condensation product. The tertiary amide used includes, for example, N,N-dimethylformamide, N,N-dimethylacetoamide, N-methylpyrrolidinone, N,N-dimethylimidazolidinone and hexamethylphosphoryltriamide. The tertiary amine includes pyridine, quinoline, triethylamine and N,N-dimethylaniline. As a catalyst, N,N-dimethylformamide or pyridine is preferable. The amount of the catalyst used is preferably 0.001 to 1 mol, and more preferably 0.01 to 0.2 mol based on 1 mol of a compound for starting material. The starting material herein referred to means a compound represented by Formula (I), (IV), (V) or (VI). The catalyst is preferably used in an amount as small as possible under conditions that the reaction proceeds smoothly, since the catalyst needs to be removed after reaction.

Manufacturing in the invention can be carried out in various organic solvents. The organic solvent used includes, for example, acetonitrile, toluene, ethyl acetate, xylene, dioxane, chloroform and n-hexane, but is not limited thereto. The organic solvent used is preferably toluene.

The chemical reaction in the manufacturing method of the invention is promoted by heating. The reaction temperature is in the range of $-20°$ to $150°$ C., but it is preferably controlled according to reactivity of starting material or a halogenating agent used in the chemical reaction. It is preferable in view of yield that a hydroxy group is substituted with a halogen atom at lower temperature (for example, $-20°$ to $80°$ C.), and then amidation or esterification is carried out at elevated temperature (at a temperature higher than in the halogenation). When a 1-hydroxy-4-(4-chloromethylphenoxy)-2-naphthoanilide derivative is prepared from a 1-hydroxy-4-(4-chloromethylphenoxy)-2-naphthoic acid derivative and an aniline derivative in toluene in the presence of phosphorus trichloride, the reaction is preferably carried out as follows:

The hydroxy group of the 4-hydroxymethyl is substituted with a chlorine atom at a temperature of $50°$ to $80°$ C., and then amidation is carried out at a temperature elevated to $90°$ to $110°$ C.

In the manufacturing method of the invention, the primary amine or secondary amine is used in an amount (theoretical) of However, when the primary amine or secondary amine used is expensive as compared with a hydroxy carboxylic acid for starting material, the amine can be used in an amount less than the theoretical amount in view of yield. To the contrary, when the hydroxy carboxylic acid for starting material is expensive and the primary amine or secondary amine used is cheap, then the amine can be used in an excessive amount. The amount of the amine used is preferably 0.8 to 1.2 times the theoretical amount.

Hereunder, typical examples of the compound manufactured according to the manufacturing method of the invention will be shown.

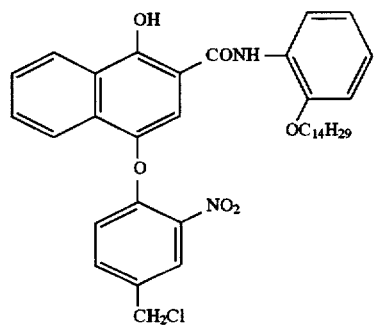

1)

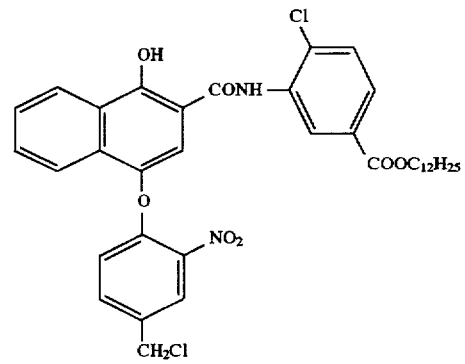

2)

-continued
3)
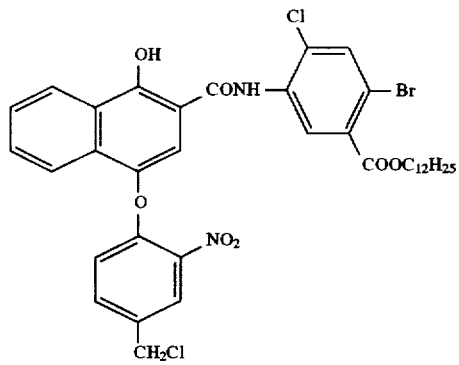
4)
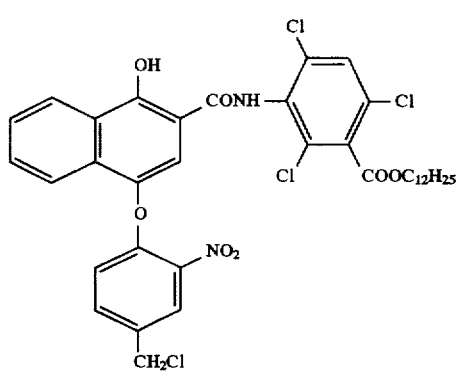
5)
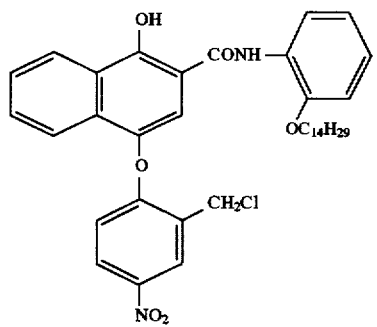
6)
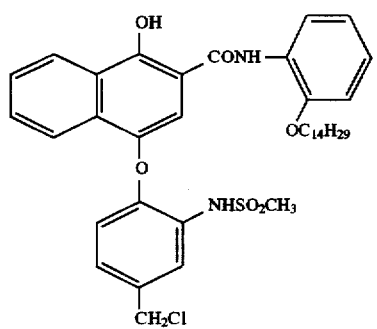
-continued
7)
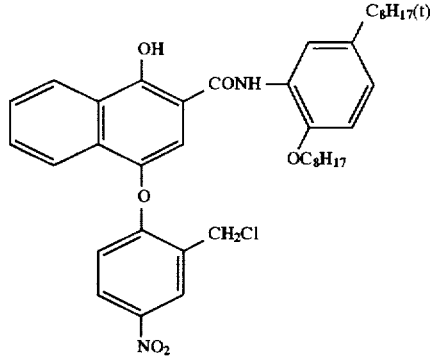
8)
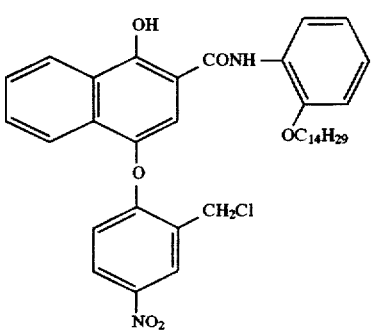
9)
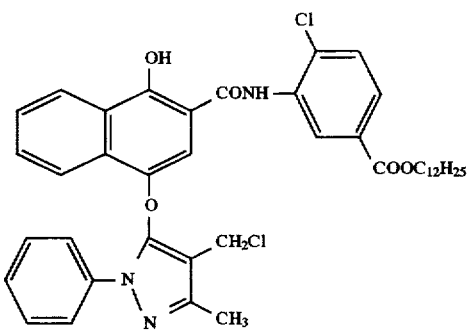
10)
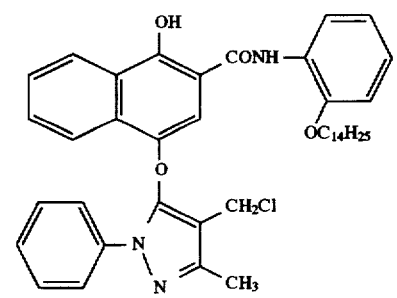
11)
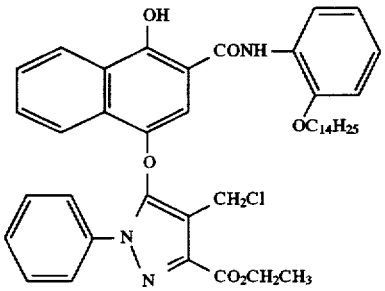

-continued
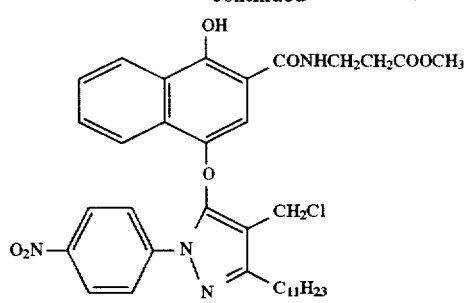
12)
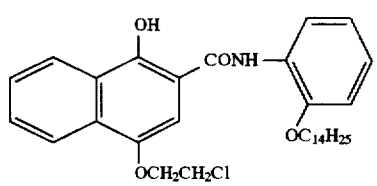
13)
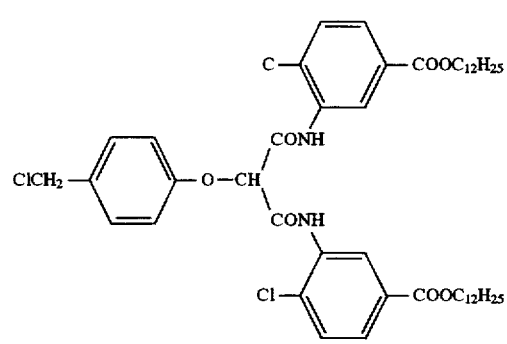
14)
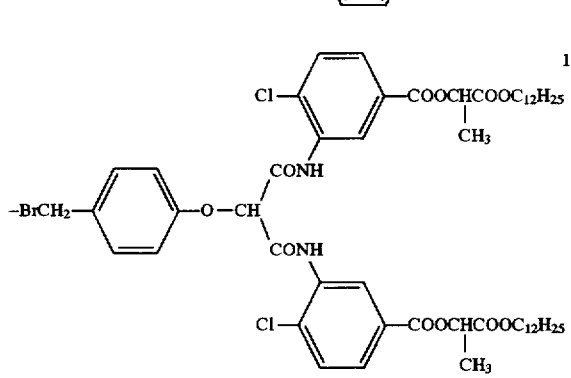
15)
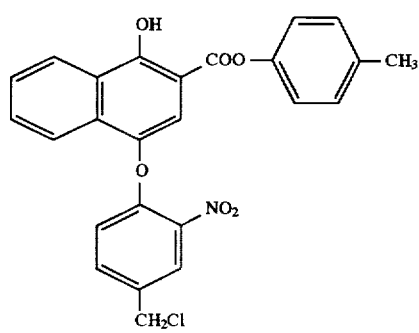
16)
-continued
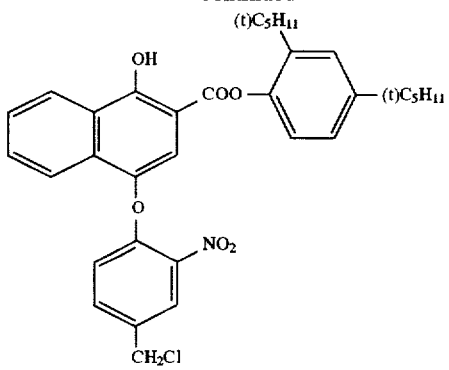
17)
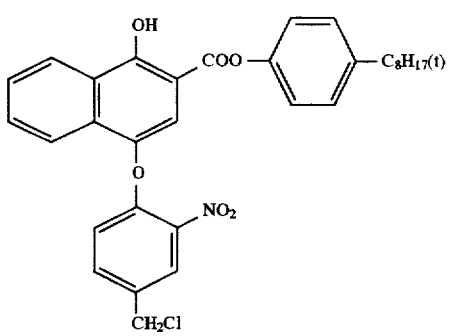
18)
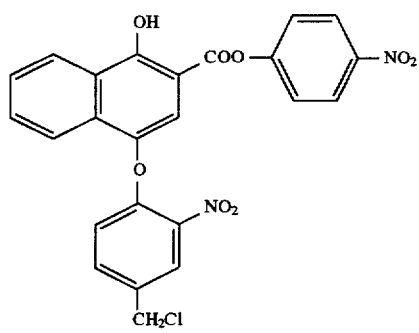
19)
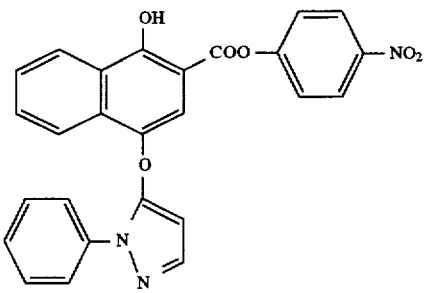
20)
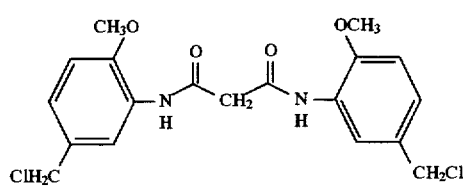
21)

-continued

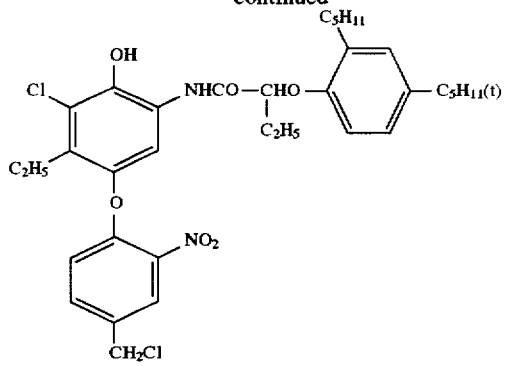

22)

EXAMPLES

Example 1

Synthesis of Exemplified compound (1)

1-hydroxy-4-(4-hydroxymethyl-2-nitrophenoxy)-2-naphthoic acid (7.00 g, 0.02 mol) and 2-tetradecyloxyaniline (6.02 g, 0.02 mol) were suspended in 70 ml of toluene, mixed with 0.35 g of pyridine and stirred. Thereafter, 2.35 g of phosphorus trichloride were added dropwise and the temperature was elevated to 60° to 65° C. and stirred for about 3 hours. Thereafter, the temperature of the resulting mixture was maintained around 100° C. and reacted for 8 hours.

Heating was stopped and the temperature of the mixture was lowered. At temperatures around 60° C., the organic phase of the mixture was twice washed with 100 ml of hot water. The resulting organic phase was filtrated to remove insoluble matter and the toluene of the filtrate was removed by distillation. The residue was recrystallized from ethyl acetate/acetonitrile. Thus, 10.4 g (yield 80%) of gray white crystal of Exemplified compound (1) were obtained.

mp 78°–94° C.

$^1$H NMR (CDCl$_3$) δ (ppm)=0.87 (3H, t, J=6.9 Hz), 1.1–1.6 (2H, m), 1.7–1.9 (2H, m), 4.05 (2H, t, J=6.9 Hz), 4.57 (2H, s), 6.77 (1H, d, J=9.0 Hz), 6.9–7.0 (1H, m), 7.0–7.1 (1H, m), 7.1–7.2 (1H, m), 7.21 (1H, s), 7.39 (1H, dd, J=2.1 HZ, J=8.7 Hz), 7.6–7.7 (2H, m), 7.8–7.9 (1H, m), 8.02 (1H, d, J=2.1 Hz), J=8.7 Hz), 8.38 (1H, dd, J=1.8 Hz, J=7.8 Hz), 8.5–8.6 (1H, m), 8.64 (1H, bs), 13.68 (1H, s)

Example 2

Synthesis of Exemplified compound (2)

1-hydroxy-4-(4-hydroxymethyl-2-nitrophenoxy)-2-naphthoic acid (53.3 g, 0.15 mol) and dodecyl 3-amino-4-chlorobenzoate (51.98 g, 0.15 mol) were suspended in 320 ml of toluene, mixed with 2.67 g of pyridine and stirred. Thereafter, 17.9 g of phosphorus trichloride were added dropwise and the temperature was elevated to 60° to 65° C. and stirred for about 3 hours. Thereafter, the temperature of the resulting mixture was maintained around 100° C. and reacted for 8 hours.

Heating was stopped and the temperature of the mixture was lowered. At temperatures around 60° C., the organic phase of the mixture was washed twice with 100 ml of hot water. The resulting organic phase was filtrated to remove insoluble matter and the toluene of the filtrate was removed by distillation. The residue was recrystallized from ethyl acetate/acetonitrile. Thus, 86.6 g (yield 83%) of gray white crystal of Exemplified compound (2) were obtained.

mp 143°–145° C.

$^1$H NMR (CDCl$_3$) δ (ppm)=0.87 (3H, t, J=6.9 Hz), 1.1–1.6 (18H, m), 1.7–1.9 (2H, m), 4.35 (2H, t, J=6.9 Hz), 4.58 (2H, s), 6.79 (1H, d, J=8.7 Hz), 7.23 (1H, s), 7.43 (1H, dd, J=2.4 Hz, J=8.7 Hz), 7.41 (1H, d, J=8.7 Hz), 7.6–7.7 (2H, m), 7.81 (1H, dd, J=2.1 Hz, J=8.4 Hz), 7.9–8.0 (1H, m), 8.05 (1H, d, J=2.4 Hz), 8.37 (1H, bs), 8.5–8.6 (1H, m), 9.04 (1H, d, J=1.8 Hz), 13.30 (1H, s)

Example 3

Synthesis of Exemplified compound (3)

1-hydroxy-4-(4-hydroxymethyl-2-nitrophenoxy)-2-naphthoic acid (10.66 g, 0.03 mol) and dodecyl 5-amino-2-bromo-4-chlorobenzoate (12.56 g, 0.03 mol) were suspended in 60 ml of toluene, mixed with 0.50 g of N,N-dimethylformamide and stirred. Thereafter, 3.58 g of phosphorus trichloride were added dropwise and the temperature was elevated to 60° to 65° C. and stirred for about 3 hours. Thereafter, the temperature of the resulting mixture was maintained around 100° C. and reacted for 8 hours.

Heating was stopped and the temperature of the mixture was lowered. At temperatures around 60° C., the organic phase of the mixture was washed twice with 100 ml of hot water. The resulting organic phase was filtrated to remove insoluble matters and the toluene of the filtrate was removed by distillation. The residue was recrystallized from toluene/acetonitrile. Thus, 18.4 g (yield 83%) of gray white crystal of Exemplified compound (3) were obtained.

$^1$H NMR (CDCl$_3$) δ (ppm)=0.87 (3H, t, J=6.9 Hz), 1.1–1.6 (18H, m), 1.7–1.9 (2H, m), 4.36 (2H, t, J=6.9 Hz), 4.58 (2H, s), 6.79 (1H, d, J=8.7 Hz), 7.19 (1H, s), 7.43 (1H, dd, J=2.4 Hz, J=8.7 Hz), 7.6–7.7 (2H, m), 7.74 (1H, s), 7.9–8.0 (1H, m), 8.05 (1H, d, J=2.4 Hz), 8.31 (1H, bs), 8.5–8.6 (1H, m), 8.91 (1H, s), 13.16 (1H, s)

Example 4

Synthesis of Exemplified compound (4)

1-hydroxy-4-(4-hydroxymethyl-2-nitrophenoxy)-2-naphthoic acid (7.10 g, 0.02 mol) and dodecyl 5-amino-2,4-dichlorobenzoate (8.18 g, 0.02 mol) were suspended in 45 ml of toluene, mixed with 0.37 g of N,N-dimethylformamide and stirred. Thereafter, 2.38 g of phosphorus trichloride were added dropwise and the temperature was elevated to 60° to 65° C. and stirred for about 3 hours. Thereafter, the temperature of the resulting mixture was maintained around 100° C. and reacted for 16 hours.

Heating was stopped and the temperature of the mixture was lowered. At temperatures around 60° C., the organic phase of the mixture was washed twice with 100 ml of hot water. The resulting organic phase was filtrated to remove insoluble matter and the toluene of the filtrate was removed by distillation. The residue was recrystallized from acetonitrile. Thus, 10.08 g (yield 66%) of gray white crystal of Exemplified compound (4) were obtained.

$^1$H NMR (CDCl$_3$) δ (ppm)=0.87 (3H, t, J=6.9 Hz), 1.1–1.6 (18H, m), 1.7–1.9 (2H, m), 4.35 (2H, t, J=6.9Hz), 4.58 (2H, s), 6.79 (1H, d, J=8.7 Hz), 7.4–7.5 (2H, m), 7.50 (1H, s), 7.6–7.8 (2H, m), 7.84 (1H, s), 7.8–7.9 (1H, m), 8.03 (1H, d, J=2.1 Hz), 8.5–8.6 (1H, m), 13.06 (1H, s).

Example 5

Synthesis of Exemplified compound (2)

Exemplified compound (2) was prepared in the same manner as in Example 2, except that pyridine was not added. The yield was less than in Example 2.

Example 6

Synthesis of Exemplified compound (16)

1-hydroxy-4-(4-hydroxymethyl-2-nitrophenoxy)-2-naphthoic acid (3.55 g, 0.01 mol) and p-cresol (1.30 g, 0.01 mol) were suspended in 30 ml of toluene, mixed with 0.1 g of DMF and stirred. Thereafter, 1.19 g (0.0087 mol) of phosphorus trichloride were added dropwise and the temperature was elevated to 60° to 65° C. and stirred for about 3 hours. Thereafter, the temperature of the resulting mixture was maintained around 100° C. and reacted for 20 hours.

Heating was stopped and the temperature of the mixture was lowered. At temperatures around 60° C., the organic phase of the mixture was washed twice with 100 ml of hot water. The resulting organic phase was filtrated to remove insoluble matters and the toluene of the filtrate was removed by distillation. The residue was purified with silica gel column chromatography. Thus, 3.43 g (yield 74%) of Exemplified compound (16) were obtained.

$^1$H NMR (CDCl$_3$) δ (ppm)=2.38 (3H, t, J=6.9 Hz), 4.57 (2H, s), 6.86 (1H, d, J=8.7 Hz), 7.1–7.2 (2H, m), 7.2–7.3 (2H, m), 7.43 (1H, dd, J=2.1 Hz, J=8.7 Hz), 7.6–7.8 (3H, m), 7.9–8.0 (1H, m), 8.03 (1H, d, J=2.1 Hz), 8.5–8.6 (1H, m), 11.76 (1H, s).

Comparative Example

Synthesis of Exemplified compound (2) (Synthesis employing dicyclohexylcarbodiimide and thionylchloride)

1-hydroxy-4-(4-hydroxymethyl-2-nitrophenoxy)-2-naphthoic acid (5.33 g, 0.015 mol) and dodecyl 3-amino-4-chlorobenzoate (5.2 g, 0.015 mol) were suspended in 30 ml of ethyl acetate, added at 0°–5° C., while cooling with ice, with a solution containing 3.03 g of dicyclohexylcarbodiimide and stirred for 2 hours. Thereafter, the mixture was stirred at room temperature overnight. The resulting mixture was filtrated to remove insoluble matters and the ethyl acetate of the filtrate was removed by distillation. The residue was purified with silica gel column chromatography. The resulting crystal was dissolved in 20 ml of ethyl acetate, added with 2.6 g of thionylchloride, and refluxed for 2 hours. The resulting organic phase was washed with water and the ethyl acetate was removed by distillation. The residue was recrystallized from ethyl acetate/acetonitrile. Thus, 2.23 g of Exemplified compound (2) were obtained.

What is claimed is:

1. A method for synthesizing a halogen-containing condensation product, the method comprising the steps of:

mixing a compound represented by Formula (I), a compound represented by Formula (II) or (III), and a halogenating agent in a solvent to obtain a mixture; and reacting the mixture so that dehydration condensation and halogenation are carried out, $$\underset{\underset{R_2}{|}}{\overset{\overset{O}{\|}}{HOC}}\text{+}L_1\text{)}_p\underset{}{C}-OH \qquad \text{Formula (I)}$$

wherein R$_1$ and R$_2$ independently represent a hydrogen atom, an alkyl group or an aryl group; L$_1$ represents an alkylene group or an arylene group; and p represents 0 or 1, $$H-N\underset{R_4}{\overset{R_3}{\diagup}}\qquad \text{Formula (II)}$$

wherein R$_3$ and R$_4$ independently represent a hydrogen atom, an alkyl group or an aryl group, $$\text{OH} \quad\text{+(R}_5\text{)}_{n^1} \qquad \text{Formula (III)}$$

wherein R$_5$ represents a hydrogen atom, an alkyl group, an aryl group, a halogen atom, a nitro group, a cyano group, an acylamino group, a carbamoyl group, an alkylsulfonyl group, an arylsulfonyl group, a sulfamoyl group, a sulfonylamino group or a heterocyclic ring; n$^1$ represents an integer of 0 to 5, provided that when n$^1$ represents 2 or more, two adjacent R$_5$ may cosine with each other to form a ring, wherein said reacting comprises substituting the hydroxy group of the —C(R$_1$)(R$_2$)—OH with halogen at a first temperature and then carrying out amidation or esterification at a second temperature higher than said first temperature.

2. The method of claim 1 wherein Formula (I) is a compound of the Formula (IV) or (V):

$$\text{Formula (IV)}$$

wherein R$_6$ represents a hydrogen atom, an alkyl group, an aryl group, a halogen atom, a nitro group, a cyano group, an acylamino group, a carbamoyl group, an alkylsulfonyl group, an arylsulfonyl group, a sulfamoyl group, a sulfonylamino group or a heterocyclic ring; n$^2$ represents an integer of 0 to 3, provided that when n$^2$ represents 2 or more, R$_6$ may be the same or different or two adjacent R$_6$ may combine with each other to form a ring; R$_7$ and R$_8$ independently represent a hydrogen atom, an alkyl group or an aryl group; L$_2$ represents an alkylene group or an arylene group; and q represents 0 or 1.

$$\text{Formula (V)}$$

wherein R$_9$ represents a hydrogen atom, an alkyl group, an aryl group, a halogen atom, a nitro group, a cyano group, an acylamino group, a carbamoyl group, an alkylsulfonyl group, an arylsulfonyl group, a sulfamoyl group, a sulfonylamino group or a heterocyclic ring; n$^3$ represents an integer of 0 to 3, provided that when n$^3$ represents 2 or more, two adjacent R$_9$ may combine with each other to form a ring; R$_{10}$ and R$_{11}$ independently represent a hydrogen atom, an alkyl group or an aryl group; L$_3$ represents an alkylene group or an arylene group; r represents 0 or 1; and Z represents an atomic group necessary to form 1-phenyl-3-methyl-5-pyrazolyl, 1-(4-nitrophenyl)-3-undecyl-5-pyrazolyl, 2-pyridyl, 2-nitro-1-phenyl, 2-methylsulfonylamino-1-phenyl, or 1-phenyl-3-ethoxycarbonyl-5-pyrazolyl.

3. The method of claim 1, wherein said reacting is carried out by heating.

4. The method of claim 1, wherein said halogenating agent is selected from the group consisting of phosphorous trichloride, thionylchloride, phosphorus oxychloride, phosphoric pentachloride, phosphorous tribromide and phosphorus oxybromide.

5. The method of claim 4, wherein said halogenating agent is phosphorous trichloride.

6. The method of claim 1, wherein said $R_1$, $R_2$ and $R_3$ independently represent a hydrogen atom; said $R_4$ represents a substituted phenyl group having 10 or more carbon atoms; and said $n^1$ is 2 and the two $R_5$ combine with each other to form a naphthalene ring with the benzene ring in said Formula (III).

7. The method of claim 2, wherein said $R_6$, $R_7$, $R_8$, $R_9$, $R_{10}$ and $R_{11}$ each represent a hydrogen atom.

8. A method for synthesizing a halogen-containing condensation product, the method comprising the step of:

mixing a compound represented by Formula (VI), a compound represented by Formula (VII) or (VIII) and a halogenating agent in a solvent to obtain a mixture; and reacting the mixture so that dehydration condensation and halogenation are carried out, Formula (VI)

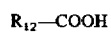

$R_{12}$—COOH wherein $R_{12}$ represents a hydrogen atom, an alkyl group or an aryl group.

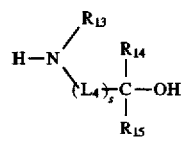

Formula (VII)

wherein $R_{13}$, $R_{14}$ and $R_{15}$ independently represent a hydrogen atom, an alkyl group or an aryl group; $L_4$ represents an alkylene group or an arylene group; and s represents 0 or 1.

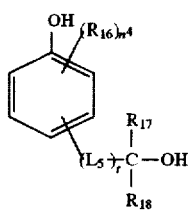

Formula (VIII)

wherein $R_{16}$ represents a hydrogen atom, an alkyl group, an aryl group, a halogen atom, a nitro group, a cyano group, an acylamino group, a carbamoyl group, an alkylsulfonyl group, an arylsulfonyl group, a sulfamoyl group, a sulfonylamino group or a heterocyclic ring; $n^4$ represents an integer of 0 to 3, provided that when $n^4$ represents 2 or more, two adjacent $R_{16}$ may combine with each other to form a ring; $R_{17}$ and $R_{18}$ independently represent a hydrogen atom, an alkyl group or an aryl group; $L_5$ represents an alkylene group or an arylene group; and t represents 0 or 1.

9. The method of claim 8, wherein said $R_{13}$, $R_{14}$, $R_{15}$, $R_{17}$ and $R_{18}$ independently represent a hydrogen atom; and said $n^4$ is 2 and the two $R_{16}$ combine with each other to form a naphthalene ring with the benzene ring in said Formula (VIII).

* * * * *